(12) United States Patent
Bousse et al.

(10) Patent No.: US 7,195,986 B1
(45) Date of Patent: Mar. 27, 2007

(54) MICROFLUIDIC DEVICE WITH CONTROLLED SUBSTRATE CONDUCTIVITY

(75) Inventors: Luc J. Bousse, Los Altos, CA (US); Seth R. Stern, Mountain View, CA (US); Richard J. McReynolds, San Jose, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 490 days.

(21) Appl. No.: 10/384,349

(22) Filed: Mar. 7, 2003

Related U.S. Application Data (60) Provisional application No. 60/362,340, filed on Mar. 8, 2002.

(51) Int. Cl.
*H01L 21/331* (2006.01)
*H01L 21/00* (2006.01)
*H01L 21/04* (2006.01)
*B01L 3/02* (2006.01)
*B32B 5/02* (2006.01)

(52) U.S. Cl. .......... 438/369; 422/50; 422/68.1; 422/81; 422/82; 422/100; 422/101; 422/102; 422/103; 422/104; 436/43; 436/63; 436/180; 29/592; 29/592.1; 29/25.01; 438/48; 438/49; 438/372; 438/373; 438/376; 438/505; 438/506; 438/510; 438/514

(58) Field of Classification Search ............. 29/592, 29/592.1, 25.01; 438/48, 49, 372, 373, 505, 438/506, 510, 514; 422/50, 68.1, 81, 82, 422/100, 101, 102, 103, 104; 436/43, 63, 436/180

See application file for complete search history.

(56) References Cited

U.S. PATENT DOCUMENTS

| 5,779,868 | A | 7/1998 | Parce et al. |
| 5,858,195 | A | 1/1999 | Ramsey |
| 5,948,227 | A | 9/1999 | Dubrow |
| 5,965,001 | A | 10/1999 | Chow et al. |
| 5,965,410 | A | 10/1999 | Chow et al. |
| 5,976,336 | A | 11/1999 | Dubrow et al. |
| 6,001,229 | A | 12/1999 | Ramsey |
| 6,090,251 | A | 7/2000 | Sundberg et al. |
| 6,153,073 | A | 11/2000 | Dubrow et al. |
| 6,271,021 | B1* | 8/2001 | Burns et al. ............. 435/287.2 |
| 2004/0201013 | A1* | 10/2004 | Faris ......................... 257/40 |

OTHER PUBLICATIONS

Gottschlich, N. et al. "Two-Dimensional Electrochromatography/Capillary Electrophoresis on a Microchip" *Anal. Chem.* (2001) 73:2669-2674.
Hosono H. et al., "Optical and electrical properties of proton-implated amorphous $SiO_2$, $GeO_2$-$SiO_2$, $MgO$-$P_2O_5$ and nanocrystalline $MgIn_2O_4$: novel materials by proton implantation" *J. Non-crystalline Solids* (1995) 182:109-118.
Khandurina, J. et al. "Microfabricated Porous Membrane Structure for Sample Concentration and Electrophoretic Analysis" *Anal. Chem.* (1999) 71:1815-1819.

(Continued)

*Primary Examiner*—Brian Sines
(74) *Attorney, Agent, or Firm*—Donald R. McKenna; Ann C. Petersen (57) ABSTRACT

A method to achieve controlled conductivity in microfluidic devices, and a device formed thereby. The method comprises forming a microchannel or a well in an insulating material, and ion implanting at least one region of the insulating material at or adjacent the microchannel or well to increase conductivity of the region.

12 Claims, 5 Drawing Sheets

OTHER PUBLICATIONS

Martin, P. et al., "Electrical surface conductivity in quartz induced by ion implantation" *J. Appl. Physics* (1992) 72:2907-2911.

Nakajima, A. et al., "Microstructure and electrical properties of Sb nanocrystals formed in thin, thermally grown $SiO_2$ layers by low-energy ion implantation" *J. Vacuum Sci. Technol.* (1999) B17:1317-1322.

Okura, T. et al., "Ionic conductivities of Na+ -ion implanted silico-phosphate glass-ceramics" *Solid State Ionics* (2000) SI:1049-1054.

Prawer, S. et al., "Conductivity in insulators due to implantation of conducting species" *J. Appl. Physics* (1993) 73:3841-3845.

Rebohle, L. et al., "Blue photo- and electroluminescence of silicon dioxide layers ion-implanted with group IV elements" *Applied Physics B-Lasers and Optics* (2000) 71:131-151.

* cited by examiner

MICROFLUIDIC DEVICE WITH CONTROLLED SUBSTRATE CONDUCTIVITY

CROSS REFERENCE TO RELATED APPLICATIONS

This application claims the benefit of U.S. Provisional Patent Application No. 60/362,340, filed Mar. 8, 2002, which is incorporated herein by reference in its entirety for all purposes.

BACKGROUND OF THE INVENTION

1. Field of the Invention

The present invention is related to microfluidic devices, and specifically to methods for modifying the conductivity of materials used in the fabrication of those devices.

2. Related Art

Microfluidic technology enables the miniaturization and automation of many laboratory processes. Devices employing microfluidic technology can integrate the power of an entire laboratory full of equipment and people into a single "lab-on-a-chip." Each microfluidic device (hereafter also referred to as a "chip") contains a network of microscopic channels, or microchannels, through which fluids can be moved and in which experiments can be performed. The design of microfluidic devices for biochemical applications involves the disciplines of fluid dynamics, biochemistry, software, and thin film manufacturing.

In microfluidic devices, the driving forces that move fluids within the channels of the device can be electrokinetic forces, pressure forces, or a combination of the two. Electrokinetic forces are typically generated by applying an electric field across a microchannel, where the direction of the field is parallel to the desired direction of fluid flow. The electric field is typically applied by placing electrodes in reservoirs at the ends of the microchannel, and applying a voltage across the electrodes with a computer-controlled power supply. The voltage applied across the electrodes produces fluid flow via one or both of the phenomena of electroosmosis or electrophoresis. Electroosmosis occurs when an electric field is applied across a channel whose surface or walls contain charged functional groups. The charge on the channel wall ionizes a thin layer of fluid near the wall. This thin layer of ionized fluid is attracted to one of the electrodes, creating a flow of ionized species toward that electrode. The flow of ionized species produces both a bulk fluid flow and an electrical current. The bulk flow rate through a microchannel can be controlled with a high degree of precision by controlling the electrical current that accompanies the flow through the microchannel. The other phenomena that produces electrokinetic flow, electrophoresis, is the movement of charged molecules or particles in a fluid subjected to an electric field. Electrophoresis can be used to move charged molecules in solution, or to separate charged molecules that have different electrophoretic mobilities (which is roughly their charge to mass ratio). Electrophoresis and electroosmosis often occur at the same time when an electric field is applied to a microchannel. Techniques have been developed for minimizing one electrokinetic force while maintaining the other, as appropriate, for a given application. Precise control over fluid flow within microchannels requires precise control of the driving forces, such as electrokinetic or pressure forces. Precise control over fluid flow also requires precise engineering of the microchannels themselves because fluid flow also depends on channel geometry and surface properties.

Microfluidic devices are typically fabricated by etching or embossing grooves into a substrate, and then affixing a cover to the substrate to form the microchannels. In most microfluidic devices that employ electrokinetic flow, both the substrate and the cover plate are made of an insulating material such as glass. Insulating materials help reduce the electrical current leakage between microchannels. By reducing current leakage between microchannels, the use of insulating materials allows an increased packing density of components, such as microchannels, in a microfluidic device.

In some applications, it may be advantageous to allow a localized leakage of current between different channels in a microfluidic device. The leakage of current between channels allows the electrical currents that drive electrokinetic flow to flow in directions other than parallel to the length of the microchannels. In other words, having a conductive path between channels provides the ability of initiating electrokinetic flow in directions other than along the length of a channel. For example, fluid could be made to flow into the sidewall of a channel. Microfluidic devices with a conductive path between channels could provide advantages over standard microfluidic devices in the areas of sample concentration and two-dimensional separation.

One set of researchers has fabricated microfluidic devices that employ electrical current leakage between microchannels for the purpose of concentrating samples. Khandurina, J., et al., *Anal. Chem.* 71, pp. 1815–1819 (1999). In these microfluidic devices, the current leaks between microchannels through a porous membrane. The porous membrane is a separate layer of material sandwiched between the cover plate and substrate of a microfluidic device. In the devices shown in Khandurina, fluid from a main channel that terminates at a "T" shaped intersection with a separation channel is made to flow straight into the opposing wall of the "T" shaped intersection by allowing electrical current to flow into the opposing wall through a porous membrane above the wall. By flowing sample from the main channel into the opposing wall, the sample accumulates, and thus concentrates, at the "T" intersection. When enough sample has accumulated at the intersection, the sample is directed to flow down the separation channel. The device in Khandurina could be useful in assays in which a sample to be separated into components must be concentrated in order to increase the concentration of at least some of the components above a detectable threshold.

There are several problems with microfluidic devices that employ porous membranes to provide conductive paths between microchannels. First, the lifetime of these devices is short and unpredictable due to the nature of the porous membrane. Second, the resistance of the porous membranes may change with time. Third, the process for fabricating porous membranes lacks the dimensional control needed to fabricate porous membranes between closely spaced microchannels. Fourth, the nature of the conductivity of the porous membrane is not certain, and that could lead to unexpected fluctuations of conductivity both between and within microfluidic devices. Finally, having a conductive path between microchannels may prevent the manufacture of devices with densely packed microchannels.

Given the limitations of porous membranes, it is desirable to have an alternative method of providing conductive paths between microchannels in a microfluidic device. It would be particularly desirable if the conductive paths could be provided in a way that does not require the addition of an extra layer of material, such as the above-described layer of a porous membrane material, to the microfluidic device structure. Furthermore, it would be desirable that the dimensions of the conductive paths be able to be precisely and accurately defined. It would also be desirable that the degree of conductivity between channels be controllable. In its various aspects, embodiments of the present invention provide these and other advantages over currently known methods of allowing current to flow between the channels of a microfluidic device.

BRIEF SUMMARY OF THE INVENTION

The present invention is directed to a microfluidic device comprising at least two microchannels formed from grooves in an insulating substrate, and at least one ion implanted region in the insulating substrate located between the grooves forming the microchannels, the at least one ion implanted region having increased conductivity compared to the insulating substrate.

The present invention is also directed to a method to achieve controlled substrate conductivity in microfluidic devices, and devices formed thereby. The method comprises forming a microchannel in an insulating substrate, and ion implanting at least one region of the insulating substrate at or adjacent the microchannel to increase conductivity of the region. In some embodiments of the invention, the insulating substrate is a silica-based material, whereby the ion-implanting step increases the conductivity of the silica-based material in at least one region. In alternative embodiments, the insulating substrate is a polymer material, whereby the ion-implanting step increases the conductivity of the polymer material in at least one region.

By providing regions where substrate conductivity is increased, it is possible to run loading currents through the substrate, and thus accumulate sample components. The ion-implantation process used in embodiments of the invention can accurately and precisely modify the conductivity of small areas of an insulating substrate, so that the invention may be employed on a microfluidic device with closely packed microchannels.

These and other advantages and features will become readily apparent in view of the following detailed description of the invention.

BRIEF DESCRIPTION OF THE DRAWINGS

The features and advantages of the present invention will become more apparent from the detailed description set forth below when taken in conjunction with the drawings in which like reference numbers indicate identical or functionally similar elements. Additionally, the left-most digit of a reference number identifies the drawing in which the reference number first appears.

DETAILED DESCRIPTION

Embodiments of the present invention will now be discussed in detail. While specific features, configurations and arrangements are discussed, it should be understood that this is done for illustration purposes only. A person skilled in the relevant art will recognize that other steps, configurations and arrangements may be used without departing from the spirit and scope of the invention. It should be appreciated that the microfluidic devices in accordance with the present invention can be used to perform a variety of experiments and operations, and thus the techniques described herein could be used in connection with devices for such other functions.

Figure 1:
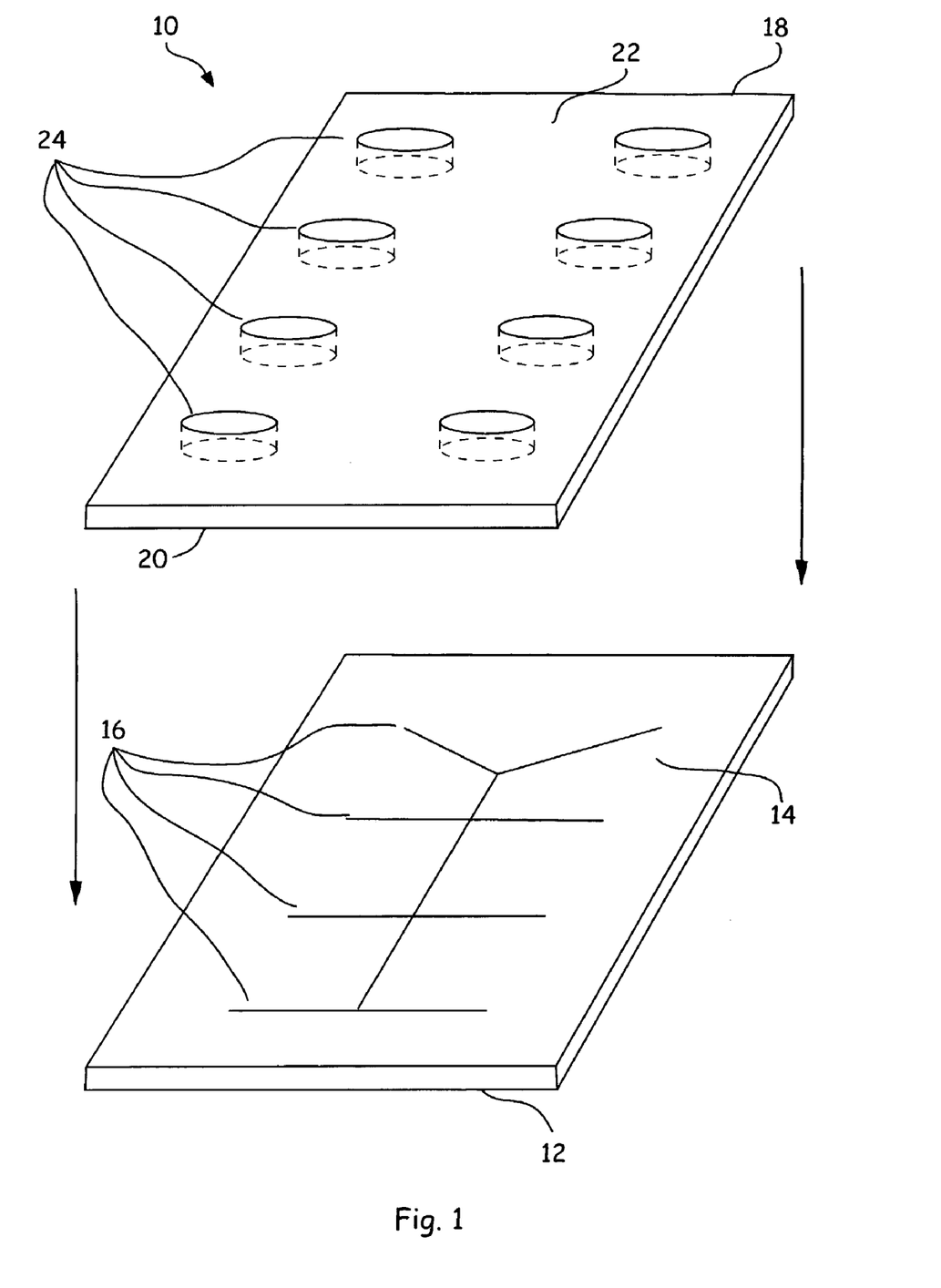
FIG. 1 is an exploded view of a microfluidic device in accordance with the invention.

An exploded view of a microfluidic device in accordance with the invention is shown in FIG. 1. The microfluidic device 10 comprises two layers: a substrate 12 and a cover plate 18. The substrate 12 may be made of a variety of materials, including quartz, glass, polymer, ceramic or even semiconductor materials. The substrate 12 comprises a pattern of grooves 16 on the upper surface 14 of the substrate. The pattern of grooves 16, when enclosed by the cover plate 18, will form the pattern of microfluidic channels in the assembled microfluidic device. The pattern of grooves may be formed by a variety of manufacturing methods, many of which are used in the semiconductor industry. For example, the pattern of grooves may be formed by embossing the pattern onto a polymer substrate, injection molding a polymer into a substrate containing the pattern, or by a combination of lithography and etching. In one embodiment, the pattern of grooves 16 is defined using a lithography process, and etched into the substrate using a wet etch process. A process combining lithography and wet etch is able to create highly precise microchannels with dimensions that can be varied by width and depth. A typical microchannel is roughly 50 μm wide and 10 μm deep.

After the pattern of grooves 16 is formed on the top surface 14 of the substrate 12, a cover plate 18 is fused with the substrate 12. Such fusion can be performed using a variety of known bonding techniques, including thermal and anodic bonding. The cover plate 18 may be formed from a variety of materials, including quartz, glass, polymer, ceramic or semiconductor materials. The cover plate 18 encloses the pattern of grooves 16 formed in the substrate 12 and converts them to microfluidic channels, or microchannels. Either or both of the substrate 12 or cover plate 18 may include holes or apertures disposed therein. In the embodiment shown in FIG. 1, holes 24 in the cover plate 18 form reservoirs or wells that are disposed above and fluidly connected to the unintersected termini of the grooves in the substrate 12. Fluids may be introduced into the microchannels of the assembled microfluidic device through these reservoirs. The size of an assembled microfluidic device can vary from less than one inch to a few inches on a side. The assembled devices are typically packaged in plastic holders, which make them easier for the user to handle.

Other embodiments of microfluidic devices are compatible with the present invention. For example, instead of only having holes in the cover layer, microfluidic devices in accordance with the invention may have holes disposed through the substrate or through both the substrate and cover plate. The extra holes could either provide separate reservoirs on opposing sides of the microfluidic device or provide through-holes that provide fluid access to the channels of the device. Embodiments of microfluidic devices employing holes in the substrate or both the substrate and cover layer are in U.S. Pat. Nos. 5,779,868 and 6,090,251, both of which are assigned to the assignee of the present invention. Other embodiments of microfluidic devices that are compatible with the present invention include multilayer microfluidic devices, which comprise two or more substrate layers. The microchannel formed in the various layers of a multilayer microfluidic device can be interconnected using vias or through-holes.

Microfluidic devices, or chips, are currently commercially available in two basic formats: planar and sipper. In planar chips, such as the chip shown in FIG. 1, the user introduces all chemical reagents, including samples, into reservoirs on the chip. Planar chips are sold for use with the Agilent 2100 Bioanalyzer system. These chips include the LabChip® DNA Analysis, RNA Analysis, Protein Analysis and Cell Fluorescence Analysis chips, which are manufactured by Caliper Life Sciences Inc., of Mountain View, Calif. Because samples are deposited into separate reservoirs in planar chips, the number of samples that can be analyzed by a planar chip is typically limited by the number of sample reservoirs provided on that chip. While planar chips could be washed and potentially reused, they are generally discarded after use.

Sipper chips are designed to analyze a large number of samples, which makes sipper chips useful for high throughput applications. In the sipper chips, minute quantities of a large number of samples can be tested in a single chip. The samples are introduced into the capillary one after the other, spaced by buffer solution. The samples then proceed through the microchannel network in a continuous flow, assembly-line fashion. A typical sipper chip employs one or more integrated sample accession capillaries for interfacing with an external collection of sample sources, such as a multiwell plate. The sample accession capillary is typically a small glass tube inserted into the substrate portion of the chip. Embodiments of sipper chips compatible with the present invention are described in U.S. Pat. No. 5,779,868, which is assigned to the assignee of the present invention. Commercially available sipper chips include chips used by the Caliper AMS 90 and 250 HTS systems.

In most microfluidic devices, fluids are moved through the microchannels of the device by means of electrokinetic forces, pressure forces, or a combination of the two. Electrokinetic forces are typically generated by applying an electric field along the length of a microchannel, parallel to the desired direction of fluid flow. For example, in the microfluidic device 10 in FIG. 1, electrokinetic driving forces would be applied to the microchannels, which are formed by enclosing the grooves 16, by placing electrodes in the reservoirs 24 and applying voltages between the various electrodes. Fundamental techniques for controlling electrokinetic flow in the microchannels of a microfluidic device were invented by Dr. J. Michael Ramsey. These techniques are covered by a series of issued and pending patents, including U.S. Pat. Nos. 6,001,299 and 5,858,195. Dr. Ramsey's techniques control fluid flow within multiple microchannels by simultaneously applying separately controllable electric fields across the different microchannels. Software programs can be written for computer controlled power supplies to generate highly specific and complex networks of flow within a network of microchannels.

This invention is directed to using ion-implantation to controllably and locally increase the conductivity of a substrate or cover plate of a microfluidic device. By increasing the conductivity in a defined area, a path for electrical current can be defined between microchannels. The physical separation distance between microchannels in a microfluidic device in accordance with the invention can range from between 10–100 µm, and in most embodiments between 20 to 50 µm. The ion-implantation process provides control over the conductivity of the region of the microfluidic device being implanted by controlling the dose, energy, and subsequent thermal annealing of that region. Ion-implantation enables localized high-conductivity areas to be formed on a chip without degrading performance elsewhere on the chip.

As will be described below, ion implanting according to the present invention can be performed in various areas or regions of the substrate and/or cover plates of a microfluidic device. When referencing the ion implanting of an area or region, the terms "adjacent a microchannel" and "adjacent a reservoir", or the like phrases, are used herein to mean a variety of possible relative positioning of the ion implanted area or region and a microchannel and/or reservoir. As examples, "adjacent" can mean that the ion-implanted region: fully or partially overlaps (i.e., is fully or partially integral) with a portion of a microchannel and/or reservoir; or is separated a distance from a portion of a microchannel and/or reservoir. Such a separation distance or overlap will be implementation dependent.

Various authors have described methods to change the conductivity of glass (or of fused silica) by ion implantation (see Okura, T., and Yamashita, K, *Solid State Ionics* 136 SI:1049–1054 (2000); Rebohle, L., et al., *Applied Physics B-lasers and Optics* 71:131–151 (2000); Nakajima, A., et al., *J. Vacuum Sci. Technol.* B 17:1317–1322 (1999); Hosono, H., et al., *J. Non-crystalline Solids* 182:109–118 (1995); Prawer, S., et al., *J. Appl. Physics* 73:3841–3845 (1993); and Martin, P., et al., *J. Appl. Physics* 72:2907–2911 (1992)). Examples of implanted species that have been used are: protons, sodium, antimony, silicon, germanium, carbon, titanium, and chromium. Ion implantation allows accurate control of dose and depth, and has long been a vital part of silicon integrated circuit technology, where such control is essential. The details of ion implantation techniques, including thermal annealing and the manufacturing equipment to carry out ion implantation would be apparent to a person skilled in the relevant art.

To localize the effect of an ion-implantation process, some form of masking is typically used. This masking can be accomplished using lithography techniques that employ either positive or negative photoresist materials. Such lithography techniques are commonly used in the integrated circuit industry, and have been applied in the manufacture of flat panel displays, circuit boards, microfluidic devices, and various integrated circuits. When a lithography process is used to pattern a substrate, the substrate is first coated with one or more layers of a photoresist material. In some embodiments, the substrate may be coated with a layer of chrome before the photoresist is applied. The chrome may act as an adhesion layer between the photoresist and substrate materials to which the photoresist does not adequately adhere. The substrate is then placed in an aligner, in which the substrate is placed on a stage and held in place by a chuck. The chuck is typically a vacuum or electrostatic chuck capable of securely holding the substrate in place. The photoresist on the substrate is exposed to an image projected onto its surface by passing radiation through a patterned mask or reticle. As is known to those skilled in the relevant art, the radiation could be visible light, UV light, x-rays, ions, or electrons.

The projected image produces changes in the characteristics of the coating of photoresist material. These changes occur in the portions of the photoresist that were exposed to radiation during exposure. Subsequent to exposure, the layer is developed to produce a patterned layer of photoresist. In some embodiments, the substrate covered with the patterned layer of photoresist is then subjected to an etching process. Some areas of the photoresist pattern expose the underlying substrate from the etching process, while other portions of the pattern shield the substrate from the etching process. Accordingly, the photoresist pattern is effectively transferred to the underlying substrate. As previously discussed, this combination of lithography and etching can be used to form grooves in a glass or polymeric substrate that, when covered, become the microchannels of a microfluidic device. In another aspect of the invention, a photoresist pattern formed by a lithography process is used to shield portions of a substrate or cover plate from an ion implantation process.

As the size of a substrate increases, the equipment required to pattern the entire substrate at once becomes more expensive. So rather than expose the entire substrate at one time, sub portions of the photoresist layer are exposed one at a time. A special type of aligner known as a "step-and-scan" aligner is designed to expose only a portion of a substrate at a time. A step-and-scan aligner contains a projection optics system that has a narrow imaging slot. An entire substrate can be exposed by placing the imaging slot and reticle over different portions of the substrate. To accomplish this, the stage on which the wafer sits is then moved between exposures to allow multiple copies of the reticle pattern to be exposed over the substrate surface. In this manner, the sharpness of the image projected onto the substrate is maximized. Using a step-and-scan technique generally assists in improving overall image sharpness. For more background see, Nonogaki et al., "Microlithography Fundamentals in Semiconductor Devices and Fabrication Technology" (Marcel Dekker, Inc.; New York, N.Y. 1998). Step-and-repeat and field stitching lithography techniques can also be used.

Figure 2:
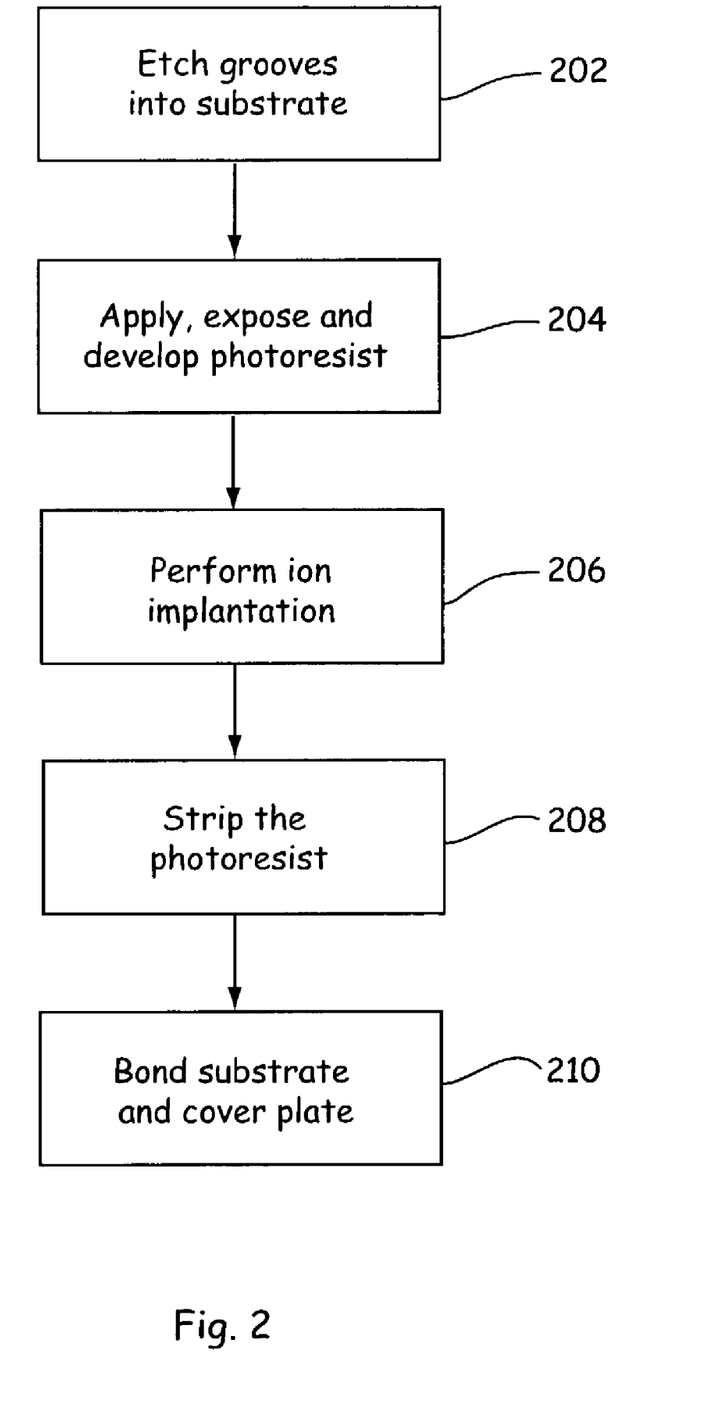
FIGS. 2 and 3 illustrate methods of forming regions of increased conductivity in microfluidic chips in accordance with the present invention.

An exemplary method for modifying the conductivity of a portion of a microfluidic device is shown in FIG. 2. This method employs the lithography and ion implantation processes described above. For clarity, the method in FIG. 2 will be described in terms of its application to the glass substrate portion of a microfluidic device. One skilled in the relevant art would recognize that methods in accordance with the invention could be applied to other portions of a microfluidic device, such as a cover plate, and could be applied to substrates and cover plates made of materials other than glass.

The first step in the method of FIG. 2 is the fabrication of the pattern of grooves in the substrate that will, when covered, form the microfluidic channels in a microfluidic device. The pattern of grooves is formed in step 202 by means of the combination of lithography and etching described above. The substrate is made of an insulating material such as glass, a silica-based material or a polymeric-based material. Before proceeding to the next step, any residual layers, such as chrome and photoresist, are removed using known techniques.

In a step 204, a thick photoresist such as Shipley SPR 220 or Clariant AZ EXPLOF 5000 is applied and patterned by exposing and developing the photoresist. In some embodiments it may be advantageous to soft bake the photoresist after it is applied to the substrate. The portions of this layer of photoresist that are not removed during the developing process will shield the portions of the substrate they cover from the ion implantation process in a step 206. In some embodiments it may be advantageous to hard bake the photoresist after it is developed. During ion implantation 206, the exposed portions of the substrate, i.e. the portions of the substrate not covered by photoresist, will have their conductivity increased by the implantation of ions. The portions of the substrate with increased conductivity regions are also referred to herein as "glass resistors." The degree to which the conductivity of the glass resistors increases during ion implantation depends on the dose and energy of the implanted ions. After ion implantation is complete, the photoresist layer is stripped away 208. Due to possible hardening of the photoresist during ion implantation, especially during high dose implants, stripping the photoresist 208 may require plasma treatments in addition to the standard wet chemical baths. As would also be apparent to a person skilled in the relevant art, it may be desirable to thermally anneal the substrate to repair damage to the substrate and to electrically activate the implanted ions. Finally, at a step 210 the substrate, which now comprises a pattern of grooves and one or more glass resistors, is bonded to a cover plate.

To completely avoid the problems associated with hardening of photoresist during ion implantation, a material other than photoresist may be used to shield portions of the substrate from the ion implantation process. In other words, a layer of material could be deposited on the substrate to form a masking layer. The material forming the masking layer could be a metal, or an insulator material different than the substrate material. Specific examples of materials suitable for use as a masking layer are chrome, silicon nitrode, amorphous silicon and polysilicon. The masking layer would form a pattern that covers the portions of the substrate that are to be shielded from the ion-implantation process, and leaves exposed the portions of the substrate that are to be implanted with ions. The masking layer is typically patterned by means of a lithography process. In an exemplary embodiment, a layer of photoresist is patterned (i.e. applied, developed, and exposed) so that only the portions of the substrate that are to be covered by the masking layer are left exposed. Next, a layer of chrome is sputtered onto the substrate. Finally, the resist is stripped so that only the chrome deposited on the exposed areas of the substrate remains. The process used to deposit chrome in this exemplary embodiment is commonly known as a lift-off process. After the ion implant is carried out, the masking layer can be removed using a selective etch process so as not to affect the underlying substrate.

Figure 3:
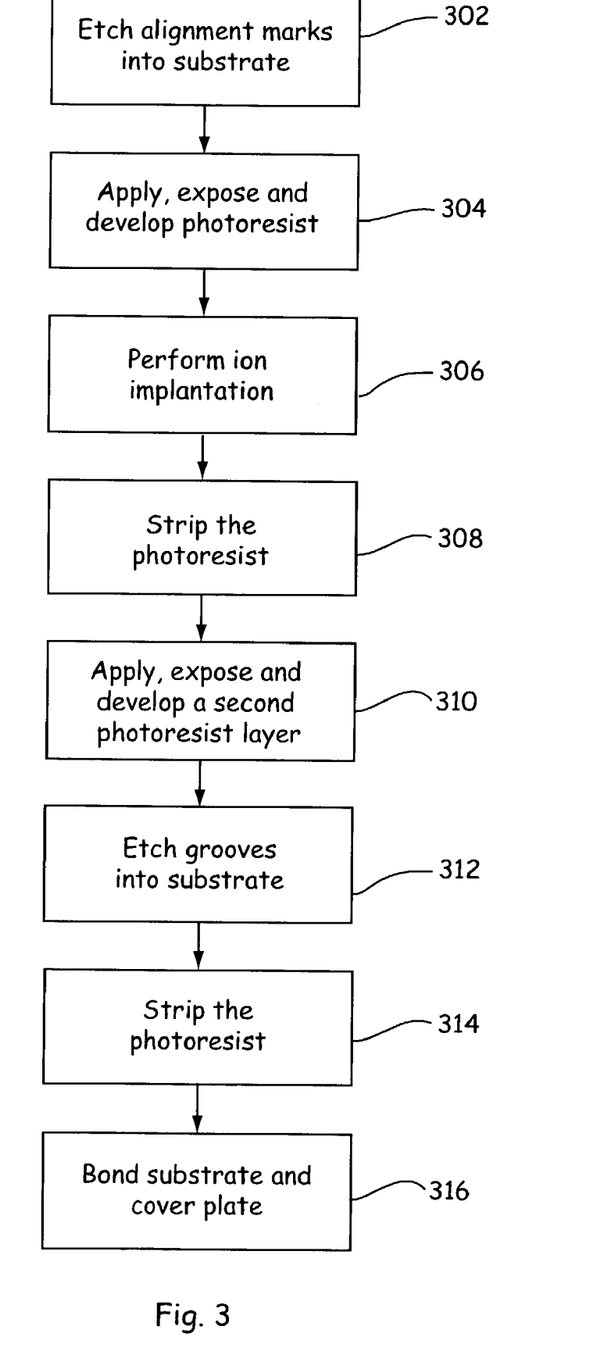

A second exemplary method for modifying the conductivity of a portion of a microfluidic device is shown in FIG. 3. In the embodiment of FIG. 3 the substrate is subjected to ion-implantation before the pattern of grooves is formed on the substrate surface. In a step 302 shallow alignment marks are etched at the edges of a substrate. These alignment marks facilitate the proper alignment of the ion-implanted regions, the glass resistors, with the yet-to-be formed pattern of grooves. In a step 304, a layer of photoresist is applied to the substrate, and is then exposed and developed. This layer of photoresist, just like the layer of photoresist in step 204 of FIG. 2, serves to shield portions of the substrate from the ion implantation process. As was discussed with regards to the layer of photoresist in FIG. 2, the photoresist in step 304 of FIG. 3 may harden during the ion implantation process. Accordingly, in some embodiments it may be desirable to replace the layer of photoresist in step 304 with a masking layer. In a step 306, ion implantation is performed to form one or more glass resistors. In a step 308 the photoresist is stripped. As discussed with regards to the embodiment in FIG. 2, it may be desirable to thermally anneal the substrate after implantation. In a step 310 a second layer photoresist is applied to substrate, and is then exposed and developed.

This layer of photoresist defines the pattern of grooves that will form the microchannels in the finished microfluidic device. In a step 312, the pattern of grooves is etched into the surface of the substrate. In a final step 314, the photoresist is stripped from the substrate. The substrate and cover plate can then be bonded together to form a microfluidic device.

In other embodiments of the invention, the conductivity of portions of the cover plate are modified by subjecting the cover plate to an ion implantation process such as one of those shown in FIGS. 2 and 3. In still other embodiments, the conductivity of portions of both the cover plate and the substrate are modified.

Glass resistors formed by ion implantation according to the present invention can be used is a variety of ways in microfluidic devices. One exemplary benefit that can be achieved by employing glass resistors in a microfluidic device is increased sensitivity in a protein assay. Glass resistors in accordance with the present invention can employed in a protein assay chip in the Agilent 2100 Bioanalyzer, for example.

Figure 4:
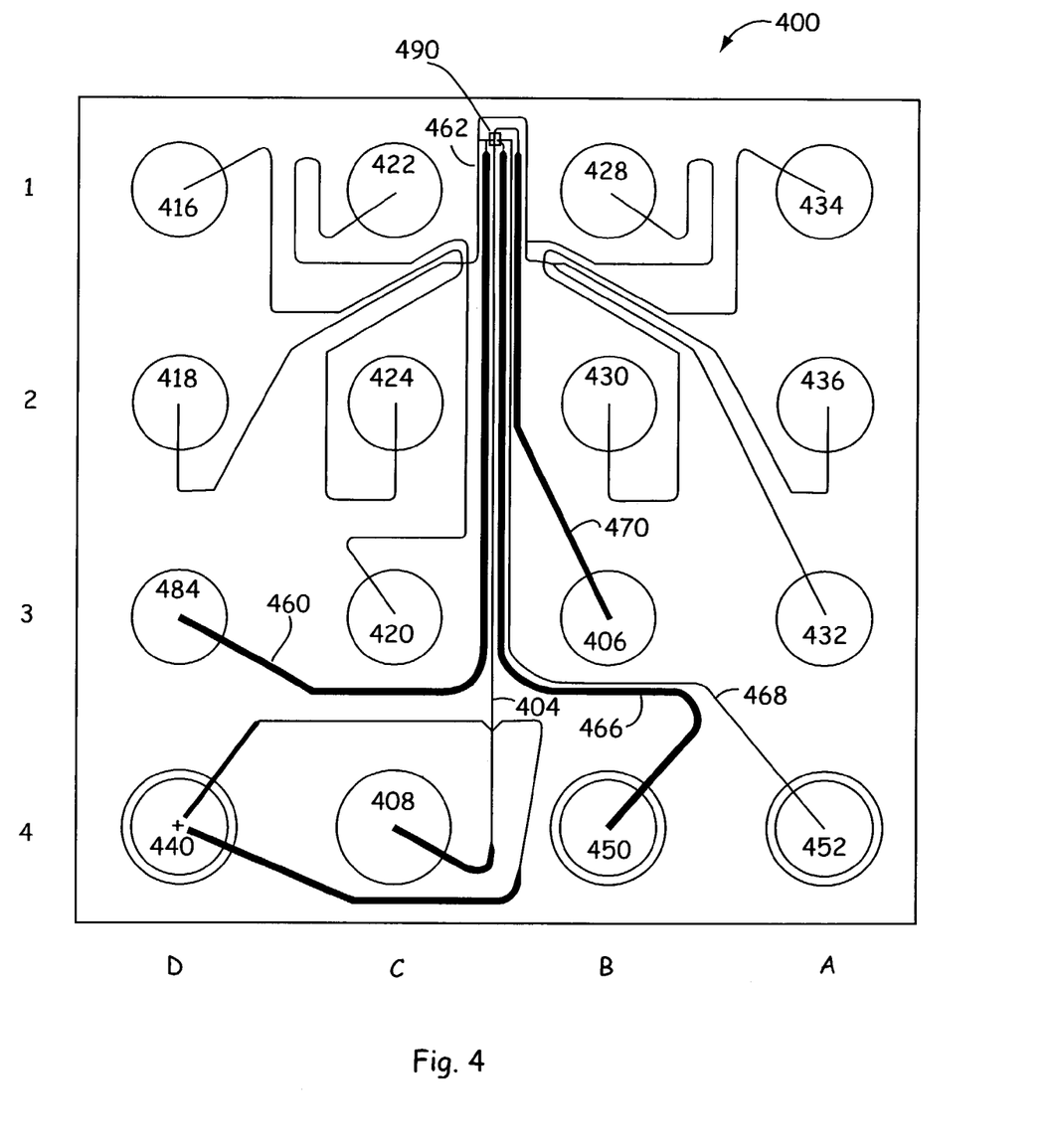
FIG. 4 illustrates a microfluidic device in accordance with the present invention.
Figure 5:
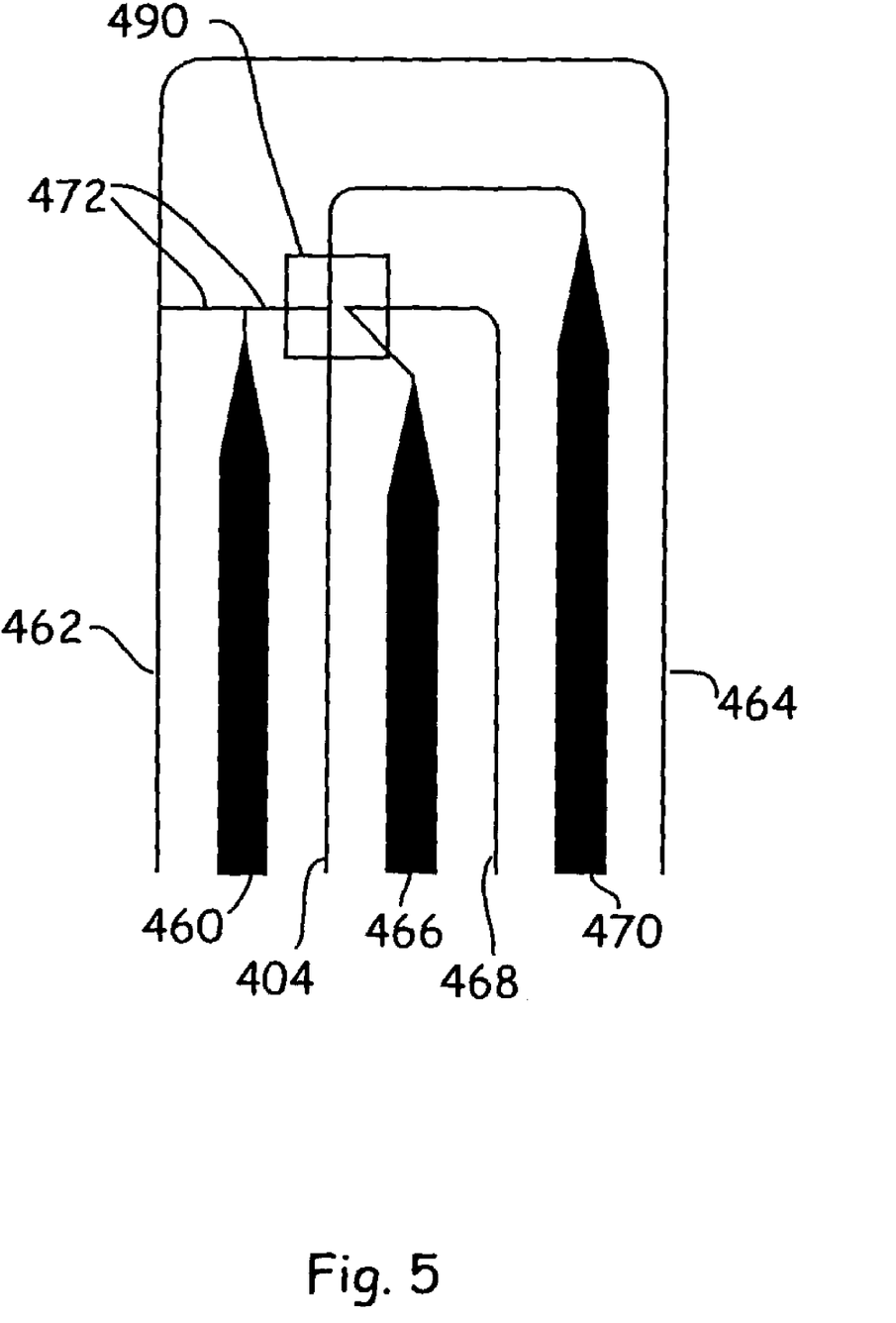
FIG. 5 is a magnified view of a portion of the microfluidic device of FIG. 4.

FIG. 4 illustrates a 16-well protein assay microfluidic chip 400 in accordance with the present invention. The wells or reservoirs 406, 408, 416–436, 440, 450, 452, 484 are in fluid communication with the network of microchannels, which includes microchannels 460–470. Of the sixteen wells, ten 416–436 contain samples to be analyzed, two 408 484 are waste wells, one 440 supplies a reagent such as a fluorescent dye that enables detection of selected species, and one 406 is a source of buffer. These fourteen wells are fluidly connected by a first network of channels. The remaining two wells 450, 452 are fluidly connected by a second network of channels. In this embodiment, the first and second networks of channels are not fluidly connected. A region of increased conductivity, a glass resistor, is shown generally at a region 490. FIG. 5 is a magnified view of the region adjacent the glass resistor 490 which is enclosed by a box for illustrative purposes.

The basic function of chip 400 is to separate a sample into its components by electrophoretic means. Means of electrophoretic separation that may be employed in embodiments of the invention are described in U.S. Pat. No. 5,948,227, which is assigned to the assignee of the present invention. In the device of FIGS. 4 and 5, the electrophoretic separation takes place in separation channel 404. Samples from wells 416–424 are injected into separation channel 404 via channels 462 and 472, while samples from wells 428–436 are injected into separation channel 404 via channels 464 and 472. The electrophoretic separation of the sample takes place as the sample travels through the separation channel 404 from the intersection of channels 472 and 404 to waste well 408. In this exemplary embodiment, only one sample at a time is separated in the separation channel 404. To improve device throughput, however, a sample can be preloaded into channel 472 while a previously injected sample is being separated in separation channel 404. The preloading process does not interfere with the separation taking place in separation channel 404 because the flow of the sample being preloaded is diverted into channel 460, which empties into waste well 484. Preloading a subsequent sample in this manner minimizes the time required to load the sample into the separation channel 404. This type of preloading is described in more detail in U.S. Pat. No. 5,948,227, and is implemented in DNA and RNA assay chips for the Agilent 2100 Bioanalyzer.

To inject a sample into the separation channel 404, the sample travels from its well through either channel 462 or 464 into channel 472. The sample is propelled through those channels by electrokinetic forces generated by voltages applied between electrodes (not shown) immersed in the sixteen reservoirs of the microfluidic device 400. When the sample arrives at the "T" intersection between channels 472 and 404, the sample is directed to travel straight out of channel 472, across channel 404, into the opposite wall of channel 404. The electrical current directing the flow of sample into the wall flows through channel 472, through the glass resistor 490, and finally through channel 468. The glass resistor allows electrical current to flow from channel 472 into channel 468, even though channels 472 and 468 are not in fluid communication. The desired electrical currents are supplied via power-supply electrodes immersed in the sixteen reservoirs of the microfluidic device 400. If, for example, the sample being injected into separation channel 404 originated from reservoir 418, the desired electric current would be generated by applying appropriate voltages to electrodes in reservoirs 418, 450, and 452. Note that voltages may have to be simultaneously applied to other reservoirs connected to the first channel network to prevent the flow of other samples into channels 462, 464 and 472, and to prevent the diversion of sample into waste well 484. Also, a voltage may have to be applied across the length of separation channel 404, by means of voltages applied to electrodes in reservoirs 406 and 408, to prevent net fluid movement along the separation channel during injection. Power supplies capable of supplying the voltages and currents required to implement this and other embodiments of the invention are described in U.S. Pat. No. 5,965,001, which is assigned to the assignee of the present invention.

As the sample is injected from channel 472 toward the opposing wall of the "T" intersection between channels 472 and 404, the sample accumulates in the portion of channel 404 near the intersection, providing a more concentrated sample. The longer the sample is concentrated in this manner, the more sample will be available for separation and detection. The degree of concentration appropriate for a given analysis will represent a simple trade-off between loading time and sensitivity. A "high sensitivity" script can be run on the same chip as a "normal" script, the only difference being a longer loading time and therefore total analysis time. By way of further example and not limitation, the technique described herein can be used in connection with the inventions disclosed in Caliper U.S. Pat. Nos. 5,976,336 and 6,153,073, both of which are assigned to the assignee of the present invention.

The increased conductivity of region 490 allows an electrical potential to be maintained across the blind "T" intersection, enabling the flow of fluid from channel 472 to be directed into a wall. The increase in conductivity can be set based on the separation between the channels between which the glass resistor provides a conductive path, and the level of ion implantation in the glass resistor. The amount ion implantation can be determined by the dose amount, the energy level used during implantation, and the thermal annealing process. In an exemplary embodiment, the sheet conductivity of a glass substrate, as measured by a four point probe, is about $10^{15}$ ohms per square ($\Omega/\square$). Ion implantation can increase the glass conductivity by several orders of magnitude, for example up to about $10^8$ $\Omega/\square$. Prawer et al., supra, shows that a sheet resistance of $10^8$ $\Omega/\square$ can be achieved by implanting carbon at a dose of $10^{16}$ ions/cm$^2$. This is a high dose, but is attainable using standard implantation methods known in the art. This level of sheet resistance is suitable for the present invention, as can be seen by the following example.

A microfluidic device similar to that shown in FIGS. 4 and 5 with 40 µm wide channels and with a gap of 100 µm between channel 490 and channels 466 and 468 can be manufactured using the methods described above. In this exemplary embodiment, the glass resistor electrically connecting channel 490 and channel 466 and 468 could have a length to width ratio of about 2 (allowing for some lateral current spreading). Assuming a sheet resistance of $10^8$ Ω/□, the resistance of the glass resistor would be $2 \times 10^8$ ohms. If the current used to inject the sample were about 3 µA, which is typical of microfluidic devices in accordance with the invention, the voltage drop across the glass resistor would be 600V. This is an easily achievable value, since the high voltage power supplies used in electrophoretic microfluidic analysis systems typically supply voltages in the range of 1500V to 3000V, as is the case with the Agilent 2100 Bioanalyzer, and the Caliper Technologies AMS-90 systems.

Exemplary Methods

Various methods can use microfluidic devices in accordance with the present invention. Such methods include, but are not limited to separating macromolecules by capillary electrophoresis and detecting reactions. Such methods employ a microfluidic device comprising an insulating substrate, at least one of a microchannel and a well formed in the insulating substrate, and at least one ion implanted region in the insulating substrate located at or adjacent the at least one of the microchannel and the well, the at least one ion implanted region having increased conductivity compared to the insulating substrate.

A method of separating macromolecules by capillary electrophoresis according an embodiment of the present invention comprises: providing a microfluidic device, as described above; introducing a sample containing the macromolecules into one end of the microchannel; and applying a voltage gradient across the length of the microchannel, whereby the macromolecules in the sample are separated in the microchannel.

A method of detecting a reaction according an embodiment of the present invention, comprises the steps of: introducing a first reagent into a microchannel of the microfluidic device; introducing a second reagent into the microchannel, whereby the first and second reagents mix together to form a reagent mixture; introducing a test compound into the reagent mixture; and detecting an effect of the compound on the reagent mixture.

Conclusion

While various embodiments of the present invention have been described above, it should be understood that they have been presented by way of example, and not limitation. It will be apparent to persons skilled in the relevant art that various changes in form and detail can be made therein without departing from the spirit and scope of the invention. This is especially true in light of technology and terms within the relevant art(s) that may be later developed. For example, the present invention is applicable in a variety of applications, such as electrical connectors for application of electrical energy, as in-line sensors for sensing conductivity, temperature, or the like. Alternatively, increased conductivity regions can be used on chips to apply or modify electric fields for various purposes. By way of further example and not limitation, the techniques described herein can be used in connection with the inventions disclosed in Caliper U.S. Pat. No. 5,965,410, which is assigned to the assignee of the present invention.

The present invention has been described above with the aid of functional building blocks, modules or steps illustrating the performance of specified functions and relationships thereof. The collection of sub-steps or boundaries of these functional building blocks have been defined herein for the convenience of the description. Alternate boundaries can be defined so long as the specified functions and relationships thereof are appropriately performed. Any such alternate collection of sub-steps or boundaries are thus within the scope and spirit of the claimed invention. Thus, the breadth and scope of the present invention should not be limited by any of the above-described exemplary embodiments, but should be defined only in accordance with the following claims and their equivalents. All publications and patent documents cited in this application are incorporated by reference in their entirety for all purposes to the same extent as if each individual publication or patent document were so individually denoted.

What is claimed is:

1. In a microfluidic device, a method to achieve controlled conductivity within a layer of the microfluidic device, the method comprising:
   forming a first microchannel in a first layer made of an insulating material;
   forming at least one of a second microchannel and a well in the first layer; and
   providing a conductive path between the first microchannel and the at least one of the second microchannel and the well by ion implanting at least one region of the first layer at or adjacent the at least one of the second microchannel and the well.

2. The method of claim 1, wherein the at least one region comprises the entire layer.

3. The method of claim 1, wherein the insulating material is a silica-based material.

4. The method of claim 1, wherein the insulating material is a polymer material.

5. The method of claim 1, wherein the first layer is a substrate of a microfluidic device.

6. The method of claim 1, wherein the first layer is a cover plate of a microfluidic device.

7. The method of claim 1, further comprising:
   bonding the first layer to a second layer of the microfluidic device.

8. The method of claim 7, further comprising:
   ion implanting at least one region of the second layer at or adjacent the at least one of the second microchannel and the well to thereby increase conductivity of the at least one region.

9. The method of claim 5, further comprising:
   bonding the first layer to a second layer of the microfluidic device.

10. The method of claim 6, further comprising:
    bonding the first layer to a second layer of the microfluidic device.

11. The method of claim 1, wherein the insulating material is glass.

12. The method of claim 11, further comprising:
    bonding the first layer to a second layer of the microfluidic device.

* * * * *